(12) United States Patent
Shifflett et al.

(10) Patent No.: US 6,841,778 B1
(45) Date of Patent: Jan. 11, 2005

(54) METHOD AND APPARATUS FOR MEASURING PARTICULATES IN VEHICLE EMISSIONS

(75) Inventors: Peter S. Shifflett, Tucson, AZ (US);
James H. Johnson, Tucson, AZ (US);
Jason K. Webster, Tucson, AZ (US);
Dennis L. Smith, Tucson, AZ (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 334 days.

(21) Appl. No.: 10/099,609

(22) Filed: Mar. 15, 2002

Related U.S. Application Data

(63) Continuation-in-part of application No. 10/039,431, filed on Nov. 9, 2001.

(51) Int. Cl.$^7$ ............................................... G01N 21/00
(52) U.S. Cl. ............................. 250/339.05; 250/339.01
(58) Field of Search ..................... 250/339.05, 339.01, 250/338.1, 336.1

(56) References Cited

U.S. PATENT DOCUMENTS

| | | | |
|---|---|---|---|
| 3,788,742 A | * | 1/1974 | Garbuny .................... 356/5.03 |
| 4,790,652 A | | 12/1988 | Uneus et al. |
| 4,924,095 A | | 5/1990 | Swanson, Jr. |
| 5,210,702 A | | 5/1993 | Bishop et al. |
| 5,246,868 A | | 9/1993 | Busch et al. |
| 5,257,087 A | | 10/1993 | Furuya |

(List continued on next page.)

OTHER PUBLICATIONS

K. Chan et al., 10 km–Long Fibre–Optic Remote Sensing of CH4 Gas by Near Infrared Absorption, Apr. 10, 1995, pp. 11–15.

Lockheed Palo Alto Research Laboratory, "A Remote Vehicle Inspection System," pp. 2–1 to 2–19.
Lockheed Palo Alto Research Laboratory, "General Description of Remove System," pp. 2–1 to 2–4.

*Primary Examiner*—David Porta
*Assistant Examiner*—Christine Sung
(74) *Attorney, Agent, or Firm*—Mintz Levin Cohn Ferris Glovsky and Popeo PC

(57) ABSTRACT

A method and apparatus for measuring particulates in vehicle emissions. An ultraviolet light beam having a predetermined wavelength, and an infrared light beam having a predetermined wavelength are propagated through the exhaust plume of a vehicle that has passed on the road. The reduction in intensities of the light beams are measured. The reduction in intensity of the ultraviolet light is due to scattering of the light by particles in the exhaust. A portion of the reduction in intensity of the infrared light is due to absorption of the light by carbon dioxide in the exhaust and a portion of the reduction in intensity is due to the scattering of light by the particles in the exhaust. To distinguish between the two, a portion of the infrared light is run through a test cell with a known amount of carbon dioxide. The reduction in intensity is measured and compared with the reduction in intensity of the infrared light passing through the exhaust plume. As one measure of particulate content, the ratio of the particles in the exhaust whose diameter is greater than said predetermined wavelength of ultraviolet light to the density of the carbon dioxide in the exhaust plume is calculated. Another measure of particulate content is the ratio of the particles in the exhaust whose diameter is greater than said predetermined wavelength of infrared light to the density of the carbon dioxide in the exhaust plume. The average size of the particles is calculated from the ratio of the particles whose diameter is greater than the predetermined wavelength of ultraviolet light to the particles whose diameter is greater that the predetermined wavelength of infrared light is calculated. The average particle size is determined from the Mie efficiency using Mie scattering and absorption theory.

44 Claims, 3 Drawing Sheets

U.S. PATENT DOCUMENTS

| | | | |
|---|---|---|---|
| 5,275,553 A | 1/1994 | Frish et al. | |
| 5,281,816 A | 1/1994 | Jacobson et al. | |
| 5,317,156 A | 5/1994 | Cooper et al. | |
| 5,319,199 A | 6/1994 | Stedman et al. | |
| 5,343,043 A | 8/1994 | Johnson | |
| 5,401,967 A | 3/1995 | Stedman et al. | |
| 5,489,777 A | 2/1996 | Stedman et al. | 250/338.5 |
| 5,498,872 A | 3/1996 | Stedman et al. | |
| 5,545,897 A | 8/1996 | Jack | |
| 5,591,975 A | 1/1997 | Jack et al. | |
| 5,621,166 A | 4/1997 | Butler | |
| 5,637,872 A | 6/1997 | Tulip | |
| 5,644,133 A | 7/1997 | Didomenico et al. | |
| 5,693,872 A | 12/1997 | Quinn | |
| 5,719,396 A * | 2/1998 | Jack et al. | 250/338.5 |
| 5,726,450 A | 3/1998 | Peterson et al. | |
| 5,767,976 A | 6/1998 | Ankerhold et al. | |
| 5,777,748 A | 7/1998 | Stengel | |
| 5,812,249 A | 9/1998 | Johnson et al. | |
| 5,821,537 A | 10/1998 | Ishihara et al. | |
| 5,831,267 A | 11/1998 | Jack et al. | |
| 5,835,211 A | 11/1998 | Wells et al. | |
| 5,877,862 A * | 3/1999 | Nelson et al. | 356/436 |
| 5,929,442 A | 7/1999 | Higashi | |
| 6,025,920 A | 2/2000 | Dec | |
| 6,028,310 A | 2/2000 | Atkinson et al. | |
| 6,061,141 A * | 5/2000 | Goldenberg et al. | 356/437 |
| 6,151,952 A | 11/2000 | Mathews et al. | |
| 6,455,851 B1 | 9/2002 | Lord et al. | 250/338.5 |
| 6,560,545 B2 | 5/2003 | Stedman et al. | 702/28 |
| 6,671,630 B2 * | 12/2003 | Stedman et al. | 702/28 |
| 2002/0010554 A1 * | 1/2002 | Stedman et al. | 702/28 |

* cited by examiner

METHOD AND APPARATUS FOR MEASURING PARTICULATES IN VEHICLE EMISSIONS

This application is a continuation-in-part of U.S. patent application Ser. No. 10/039,431, filed Nov. 9, 2001 which is incorporated herein by reference.

FIELD OF INVENTION

This invention relates to systems that use optical spectroscopy for measuring the particulate content of a gas, and particularly to an apparatus and method for determining the particulate content of the exhaust plume of a vehicle from the density of the particles in the exhaust, including particles having very small diameters, and for determining the average particle size in the exhaust.

BACKGROUND OF THE INVENTION

Motor vehicle exhaust is of great concern to the public because it is a major cause of atmospheric pollution in many areas of the country. The size of the particles in a motor vehicle exhaust plume is a significant factor in the human health impact of exhaust emissions. Particles that have a diameter less than 2.5 micron are especially harmful.

Exhaust emission opacity measures the density of particles in a vehicle's exhaust plume. Opacity meters are used to measure the opacity of the exhaust plume. To measure opacity, a beam of light is propagated across the exhaust plume of a vehicle. A light detector is positioned at the other side of the exhaust plume to measure the decrease in intensity of the light due to the particles in the exhaust plume. If there are no particles, the opacity meter will indicate zero percent opacity. As the density of particles in the exhaust increases, so does the opacity.

A disadvantage of typical opacity meters is that they must have a constant path length for the light beam that propagates through the exhaust. Also, the exhaust plume size must not change during measurement. This limits the use of typical opacity meters to direct tailpipe measurement; they cannot be used as a remote sensing tool to measure the opacity of a vehicle exhaust plume of unknown physical extent or dilution.

Another disadvantage of typical opacity meters is that they only measure the relative density of the particles, and cannot predict anything about the particle size. The very small diameter particles that are especially harmful to humans are usually invisible to the human eye. An exhaust plume that may appear "clean" to the human eye because there is no visible black emission may contain harmful sub-micron particles. In addition, almost all commercially available opacity meters use green light that has a wavelength of about 550 nanometers. As a consequence, particles that a have diameter of less than 550 nanometers will not be detected. If an exhaust plume is filled with very small particles about 200 nanometers or less, a conventional opacity meter will not measure the small particles and will report zero opacity. Yet, the small particles are very dangerous to human health.

U.S. Pat. No. 6,025,920 discloses an apparatus and method for measuring the opacity of an exhaust plume of a diesel locomotive. A single monochromatic light source is passed through the exhaust plume of a locomotive and the decrease in intensity is determined using a detector. The opacity is calculated from the decrease in intensity. This system uses infrared and ultraviolet light of relatively large wavelengths, and thus provides no information about the very small particles that are especially harmful for humans.

U.S. Pat. No. 5,257,087 discloses an apparatus and method for measuring the amount of small and large particles in a fluid contained in a test cell. The fluid is either water or chemicals that are used in the semiconductor fabrication process. The sizes of the particles are measured in order to test for impurities. A laser sends a light pulse through a test cell and a pulse counter determines, from the intensity of the light scattered by the particles, whether the particles are large or small.

U.S. Pat. Nos. 5,319,199 and 5,498,872 disclose a method and apparatus for measuring the amount of specific gas in a vehicle exhaust. Ultraviolet light is propagated across the exhaust plume of a vehicle and a detector determines the reduction in intensity of the ultraviolet light and computes the amount of nitric oxide in the exhaust. Infrared light is used to determine the amount of hydrocarbons, carbon dioxide and carbon monoxide in the exhaust. The opacity and the size of the various particles in the exhaust plume are not determined.

U.S. Pat. No. 5,835,211 discloses a single particle optical sensor for measuring the size of a particle in a liquid or gas. A light extinction method is used to determine the size of a particle that is over 1.5 $\mu$m and a light scattering method is used to determine the size of a particle as small as 0.1 $\mu$m.

Consequently, there is a need for an improved apparatus and method for determining the opacity of a vehicle exhaust plume of unknown physical plume size that accounts for small size particles in the exhaust, and for determining the average particle size in the exhaust.

SUMMARY OF THE INVENTION

The aforementioned need has been met in the present invention by providing an improved apparatus and method for measuring the particulate content of the exhaust plume of a vehicle and for determining the average size of the particles in the exhaust. An ultraviolet light beam and an infrared light beam, both having a predetermined wavelength, are propagated through the exhaust plume of a vehicle that has passed on the road. An ultraviolet light detector receives the ultraviolet light after it passes through the exhaust plume and produces a signal that is representative of the reduction in intensity of the ultraviolet light. The reduction in intensity is due to scattering of the light by particles in the exhaust, and not by absorption, because the wavelength of light does not correspond to absorption lines of any of the substances in the exhaust plume. In addition, an infrared detector receives the infrared light after it passes through the exhaust plume and produces a signal representative of the reduction in intensity of the infrared light. The density of carbon dioxide ($CO_2$) in the exhaust plume is determined from the infrared detector signal using a spectroscopic technique employing a tuneable diode laser. Using this technique, the density of $C_2$ is determined independent of the reduction in intensity due to scattering of light by particles in the exhaust.

The reduction in intensities of the ultraviolet and infrared light due to scattering are proportionally related to the densities of the particles, that is, the number of particles per unit volume. The ultraviolet detector and the infrared detector transmit the values for the reduction in intensities of the ultraviolet and infrared light to a processor which determines the density of the particles in the exhaust whose diameter is greater than the predetermined wavelength of ultraviolet light and the density of the particles in the exhaust whose diameter is greater than the predetermined wavelength of infrared light. The processor also determines the density of predetermined substance such as $CO_2$ in the exhaust plume. One measure of particulate content is the ratio of the density of the particles in the exhaust whose diameter is greater than the predetermined wavelength of ultraviolet light to the density of the $CO_2$ in the exhaust plume. Another measure of particulate content is the ratio of the density of the particles in the exhaust whose diameter is greater than the predetermined wavelength of infrared light to the density of $CO_2$ in the exhaust plume. Dividing the density of the particles by the density of the $CO_2$ accounts for differences in the size of the exhaust plume and for dilution of the exhaust plume. The dimensions of the exhaust plume are not known because the exhaust exits from the back of the tail pipe when the vehicle is traveling on the road, thus creating variable dilution and dimensions.

Scattering of the ultraviolet and infrared light is dependent on the size differential between the diameter of the particles and the wavelength of light. For a given particle size, a shorter wavelength of light will be scattered to a greater extent than a longer wavelength. Light tends to pass by particles that have a smaller diameter than its wavelength without being scattered. As a consequence, the processor calculates the ratio of the density of the particles whose diameter is greater than the predetermined ultraviolet wavelength to the density of the particles whose diameter is greater than the predetermined infrared wavelength, the ratio being characteristic of the diameter of the particles. The average particle diameter can be determined from the Mie efficiency using Mie scattering and absorption theory. The processor also calculates a particle size index, $P_s$, from the intensity measurements.

Accordingly, it is a principal object of the present invention to provide a novel and improved method and apparatus for remotely detecting the particulate content of the exhaust plume from a vehicle.

It is another object of the present invention to provide a more accurate method and apparatus for calculating the particulate content by detecting particles in the exhaust that have very small diameters.

It is a further object of the present invention to provide a novel method and apparatus for determining the average diameter of particles in the exhaust.

It is yet another object of the present invention to provide an apparatus and method for measuring the particulate content of an exhaust plume from a vehicle without having to consider the size of the exhaust plume or the path length.

The foregoing and other objects, features, and advantages of the invention will be more readily understood upon consideration of the following detailed description of the invention, taken in conjunction with the accompanying drawings.

DETAILED DESCRIPTION OF THE INVENTION

The potential ill effect of small particles in vehicle exhaust is of growing concern to the medical community. The present invention provides an apparatus and method for detecting the particulate content of exhaust plumes containing small particles so that their impact on human health can be determined.

Figure 1:
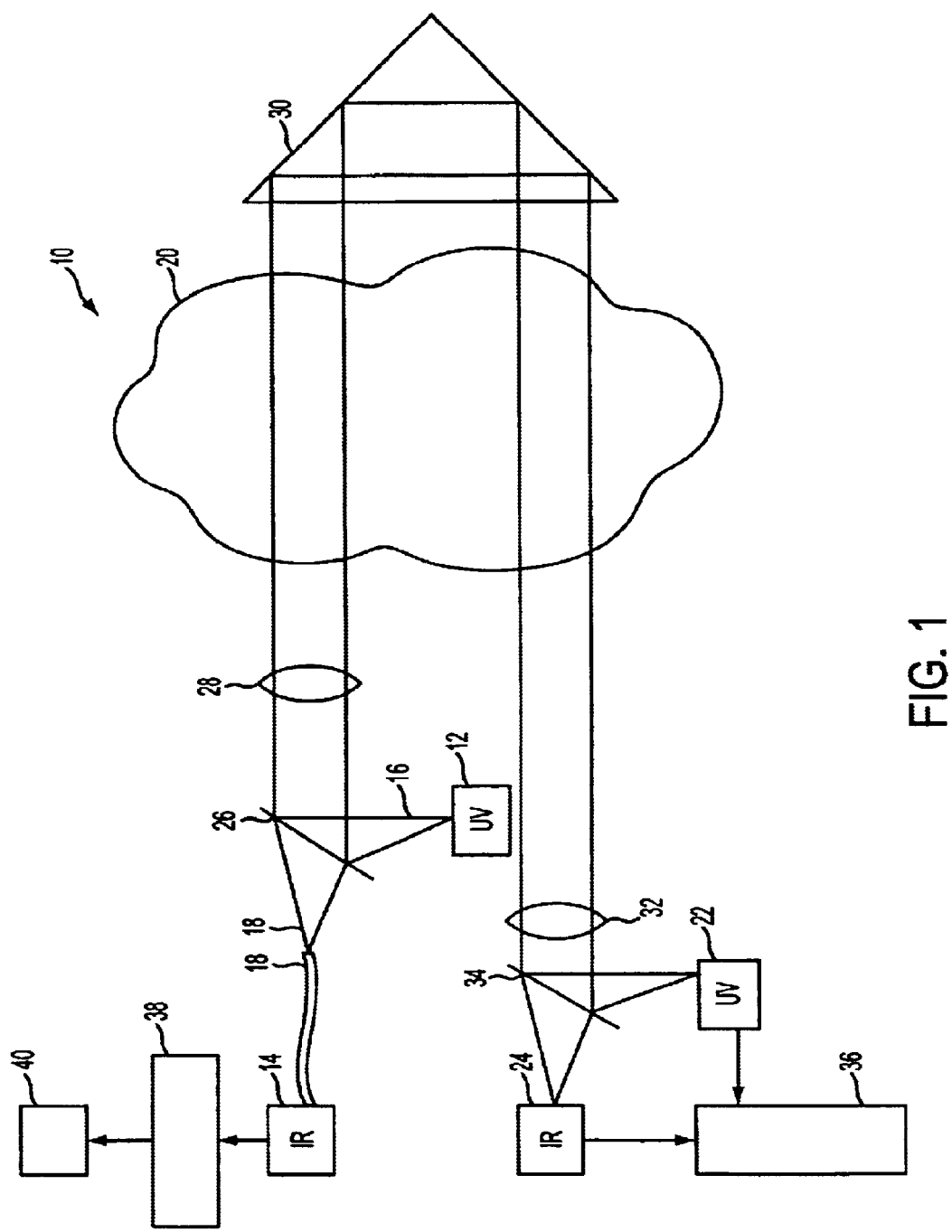
FIG. 1 is a schematic diagram of the optical pathway remote detecting apparatus for determining the density and size of particles in a vehicle's exhaust according to the present invention.

A remote sensing apparatus 10 according to the present invention that determines the particulate content and average size of particles in the exhaust plume of a vehicle is shown in FIG. 1. The sensing apparatus 10 comprises an ultraviolet light source 12 and an infrared light source 14 which respectively emit an ultraviolet light beam 16 and an infrared light beam 18 across an exhaust plume 20 of a vehicle passing in the roadway. An ultraviolet detector 22 measures the decrease in intensity of the ultraviolet light 16 after it passes through the exhaust plume 20. Similarly, an infrared detector 24 measures the decrease in intensity of the infrared light 18 after it passes through the exhaust plume 20.

The sensing apparatus 10 also includes an output beam splitter 26 which allows the infrared light 18 to pass through it toward the exhaust plume 20, and deflects the ultraviolet light 16, so that it also propagates toward the exhaust plume 20. An output lens 28 collimates the ultraviolet light 16 and the infrared light 18. Once the light passes through the exhaust plume 20, a retroreflector 30 returns the ultraviolet light 16 and the infrared light 18 back through the exhaust plume 20. An input lens 32 focuses the light to a point, and an input beam splitter 34 reflects the ultraviolet light 16 to the ultraviolet detector 22 and passes the infrared light 18 to the infrared detector 24. The ultraviolet detector 22 converts the value of the reduction in intensity of the ultraviolet light 16 to an "ultraviolet" signal and sends the signal to a processor 36. Similarly, the infrared detector 24 converts the value of the reduction in intensity of the infrared light to an "infrared" signal and sends the signal to the processor 36. The infrared light source may, for example, be a variable wavelength tunable laser diode source such as a Model Lasir manufactured by Unisearch Associates, though other infrared light sources may be used as well. The ultraviolet light source may, for example, be a simple detector, or it could be a spectrometer.

An example of how the remote sensing apparatus 10 can be used to determine the particulate content and the average particle size in the exhaust plume of a vehicle will now be explained. An ultraviolet light beam 16 having a range of wavelengths centered at about 0.23 microns is emitted from the ultraviolet light source 12. The wavelength of about 0.23 microns is selected so as to avoid any significant absorption of the light by gases such as hydrocarbons or nitric oxides in the exhaust. In this way, the reduction in intensity of the ultraviolet light is due to scattering by the particles in the exhaust rather than by absorption by the gases. Using a wavelength of 0.23 microns will enable the detector to detect particles that are as small as 0.1 microns in diameter. Although a wavelength of light around 0.23 microns is used in this example, other wavelengths can be selected without departing from the principles of the invention The ultraviolet light 16 is reflected by the output beam splitter 26 toward the exhaust plume 20. The output lens 28 collimates the ultraviolet light 16. After the ultraviolet light 16 passes through the exhaust plume 20, it is reflected back by the retroreflector 30. In this example, the ultraviolet light 16 passes once again through the exhaust plume 20, but the light 16 may pass through only once without departing from the principles of the invention. The ultraviolet light 16 passes through the input lens 32, which focuses it to a point. The input beam splitter 34 reflects the light 16 to the ultraviolet detector 22, which calculates the reduction in intensity of the ultraviolet light. This "ultraviolet" signal is passed to the processor 36, which in this example is a computer.

The amount of scattering is independent of wavelength for particles whose diameter is much larger than the light wavelength, but becomes dependent as the diameter of the particles becomes equal to or less than the wavelength. For such particles, the density of the particles is related to the change in intensity of the light that passes through the exhaust relative to the change in the intensity of the transmitted light that crosses the road before the vehicle passes. The computer 36 calculates the density of particles in the vehicle exhaust whose diameter is greater than approximately 0.23 microns from the reduction in the intensity of the light.

In addition to the ultraviolet light, an essentially monochromatic infrared light beam 16 is propagated through the exhaust plume 20 by an infrared light source 14. An infrared light beam 16 of about 1.6 microns is used to determine the density of carbon dioxide. The output beam splitter 26 passes the infrared light 16 to output lens 28, which collimates the infrared light 16. After passing through the exhaust plume 20, the retroreflector 30 returns the infrared light 16 through the exhaust plume 20, where it is focused onto the infrared detector 24 by the input lens 32. The input beam splitter 34 passes the infrared light to the detector 24, which measures the reduction in intensity of the infrared light. The "infrared" signal is then passed to the computer 36 which computes from the signal both the density of $CO_2$ in the exhaust plume and the relative concentration of particles whose diameter is greater than 1.6 microns.

Since the wavelength of infrared light is approximately 1.6 microns, it is approximately equal to the absorption line for carbon dioxide, the reduction in intensity of the infrared light is a result of both absorption and scattering. To distinguish between absorption and scattering, a portion of the infrared light 16 from the infrared light source 14 is passed through a reference cell 38 filled with a known quantity of carbon dioxide and the reduction is intensity is measured by a detector 40. The wavelength of the infrared light 16 is varied over a small range of wavelengths that correspond to the absorption lines of carbon dioxide. The reduction in intensity of the infrared light 16 is measured for these wavelengths, producing a first set of data points. In addition, infrared light 16 having the same various wavelengths is passed through the roadway before a vehicle passes, and through the exhaust plume 20 after the vehicle has passed. The reduction in intensity of the light before the vehicle passes is subtracted from the reduction in intensity from the exhaust plume to account for $CO_2$ that is already in the environment, and the reduction in intensities of the various wavelengths of infrared light 16 are measured by the infrared detector 24, thus producing a second set of data points. The second set of data points is then compared to the first set of data points.

Linear regression is used to distinguish the reduction in intensity due to absorption by the carbon dioxide from the reduction in intensity from scattering. The values for the reduction in intensity for the test cell are represented by points in one dimension, e.g., the x-axis of a Cartesian coordinate system and the values for the reduction in intensity for the exhaust plume are represented by points in an orthogonal dimension, e.g., the y-axis of the Cartesian coordinate system. Using linear regression, a line may be defined by the ordered pairs of data points, that is, one pair for each test wavelength. The slope of the line with respect to the first orthogonal dimension represents the reduction in intensity due to absorption by carbon dioxide. The computer 36 calculates the density of the $CO_2$ from this value. Mathematically, the intercept of the line in the second orthogonal direction represents the reduction in intensity due to scattering by the particles. In practice, the reduction in intensity due to scattering by particles is much greater than the reduction in intensity due to absorption. Therefore, the value for reduction in intensity of the infrared light due to scattering by the particles is equal to the reduction in intensity of the infrared light reading from the infrared detector after the vehicle has passed in the road minus the reduction in intensity of the infrared light that passes through the road before the vehicle passes.

One measure of the particulate content of the exhaust plume is calculated by taking a ratio of the density of the particles corresponding to the reduction in intensity of the ultraviolet light to the density of the carbon dioxide. The density of the particles having a diameter greater than approximately 0.23 microns is divided by the density of carbon dioxide so that the particulate content measurement can be made without having to measure the length or the dilution of the exhaust plume. In addition, since the amount of carbon dioxide is related to vehicle size, the size of a vehicle can therefore be accounted for in the particulate content calculation. In this way, an invariant particulate content measurement can be made so that vehicles of different sizes and of different degrees of exhaust dilution can be compared to one another.

Another measure of the particulate content of the exhaust plume is calculated by taking a ratio of the density of the particles corresponding to the reduction in intensity of the infrared light to the density of the carbon dioxide. The density of the particles having a diameter greater than approximately 1.6 microns is divided by the density of carbon dioxide so that, for the reasons explained above, the particulate content measurement can be made without having to measure the length or dilution of the exhaust plume.

The particulate content results can be used to determine the average particle size in the exhaust plume. Mie scattering theory is used to predict the degree of scattering and absorption in the exhaust plume as a function of the wavelength of the light, the index of refraction and the particle diameters. Mie scattering efficiency predicts how much the intensity of the ultraviolet and infrared light will be reduced after passing through the exhaust plume.

$Q(D_p, \lambda, n) = S_R/S_T$, where

Q=Mie efficiency $D_p$=particle diameter $\lambda$=wavelength n=Refractive index $S_R$=the received signal after passing through the exhaust plume $S_T$=the transmitted signal Values for the Mie efficiency, Q, as a function of particle diameter, wavelength, and refractive index are available in the literature. Mie scattering efficiency predicts the degree to which particles of a given diameter scatter and absorb light of a given wavelength. In the vehicle exhaust there are particles of different diameters. Therefore, if one assumes that there is an average particle size $\overline{D}_p$ that has a normal statistical size distribution N with a standard deviation, $\sigma$, it is possible to determine the cumulative effect of the whole range of particle size on the Mie efficiency by integrating the product of Q and N with respect to the particle diameter $D_p$.

For example, for particles of a single, fixed diameter the transmitted signal multiplied by the Mie efficiency equals the received signal after the light beam has passed through the exhaust plume:

$$S_T Q(D_p, \lambda, n) = S_R$$

For each infinitesimally small particle diameter Dp one can find the corresponding change in the transmitted signal:

$$S_T N(dD_p, \overline{D}_p, \sigma) Q(dD_p, \lambda, n) = dS_R$$

This equation can be integrated to find the total change in the transmitted signal for all the different diameter particles:

$$S_R = \int^0 N(D_p, \overline{D}_p, \sigma) Q(D_p, \lambda, n) dD_p.$$

$\overline{D}_p$ = average particle diameter $\sigma$ = the standard deviation

This equation is general for any wavelength. Since density is proportionally related to the reduction in intensity, one can take the ratio of this equation for $\lambda_1$ and $\lambda_2$ in order to account for the constant of integration.

$$R(\overline{D}_p, \sigma, n, \lambda_1, \lambda_2) = \frac{\int N(D_p, \overline{D}_p, \sigma) Q(D_p, \lambda_1, n) dD_p}{\int N(D_p, \overline{D}_p, \sigma) Q(D_p, \lambda_2, n) dD_p}.$$

In the aforementioned example, $\lambda_1$ is 0.23 microns and $\lambda_2$ 1.6 microns, but other wavelengths can also be used to determine various particle size ranges without departing from the principles of the invention. The particulate content measurement using the ultraviolet wavelength of 0.23 microns is divided by the particulate content measurement for infrared wavelength of 1.6 microns, which cancels out the density of the $CO_2$. The above ratio enables the average particle size in the exhaust plume to be calculated.

However, certain assumptions need to be made about the physical characteristics of the particles. It is necessary to know how the particles sizes are distributed such as in a normal distribution, a lognormal distribution, or a multimodal distribution. It is therefore assumed that the particle size distribution can be determined experimentally and the appropriate function used in the ratio. Also, one must have knowledge of the particle size standard deviation in the exhaust plume. The particle size standard deviation can be determined by experiment. In addition, Mie scattering theory requires knowledge of the index of refraction of the aerosol particles in the exhaust. The index of refraction used is the index of refraction of the predominant particles in the exhaust plume.

Figure 2:
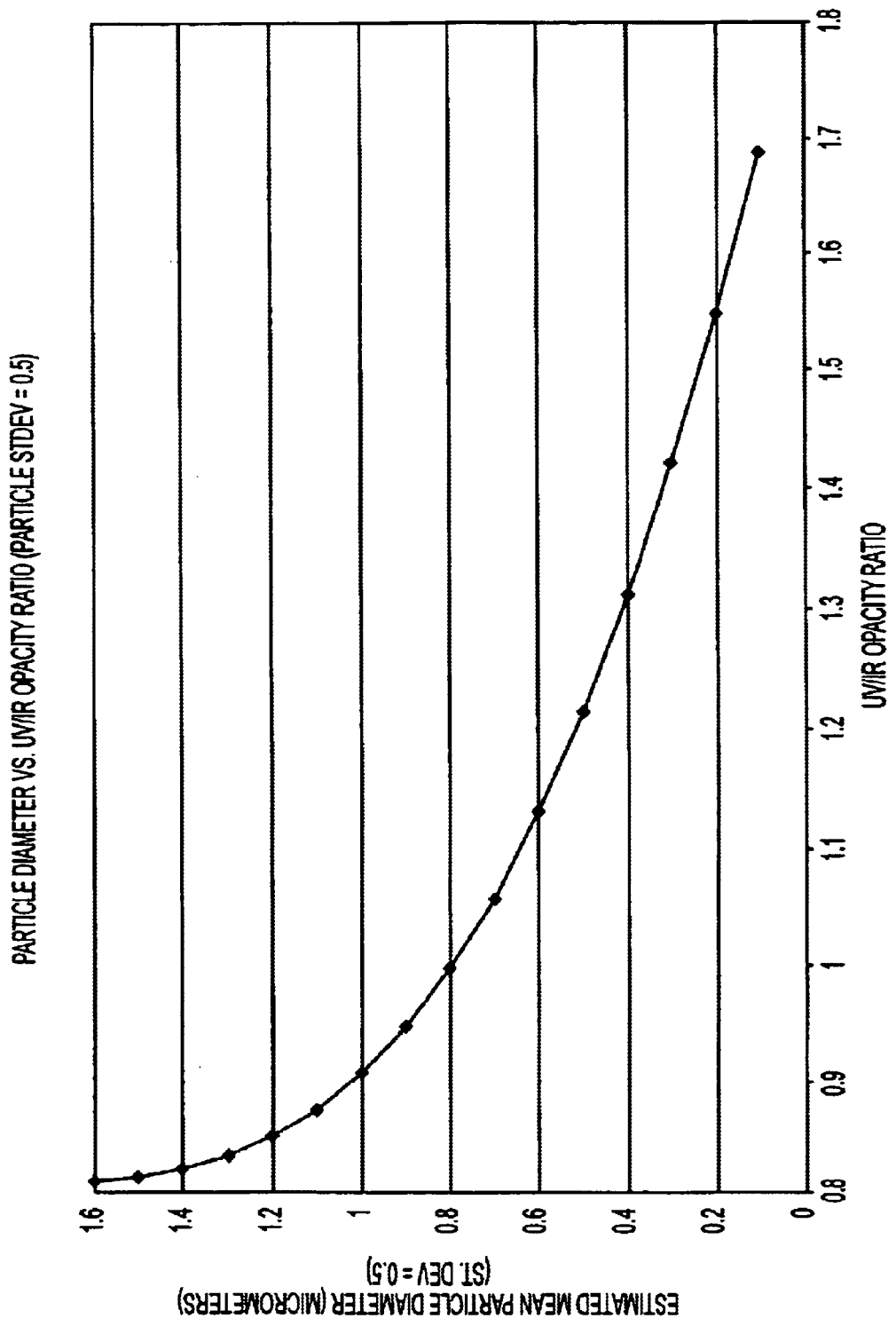
FIG. 2 is a graph of the estimated mean particle diameter for a given ultraviolet-to-infrared particulate content ratio.

FIG. 2 shows a graph of the estimated mean particle diameter as a function of the measured UV/IR particulate content ratio. This graph assumes:

1. There is a normal distribution of particles with a standard deviation of 0.5.
2. The two wavelengths used are 0.23 microns and 1.6 microns.
3. The particle index of refraction is 1.53.
4. The combined Mie scattering and absorption efficiency is assumed.

Figure 3:
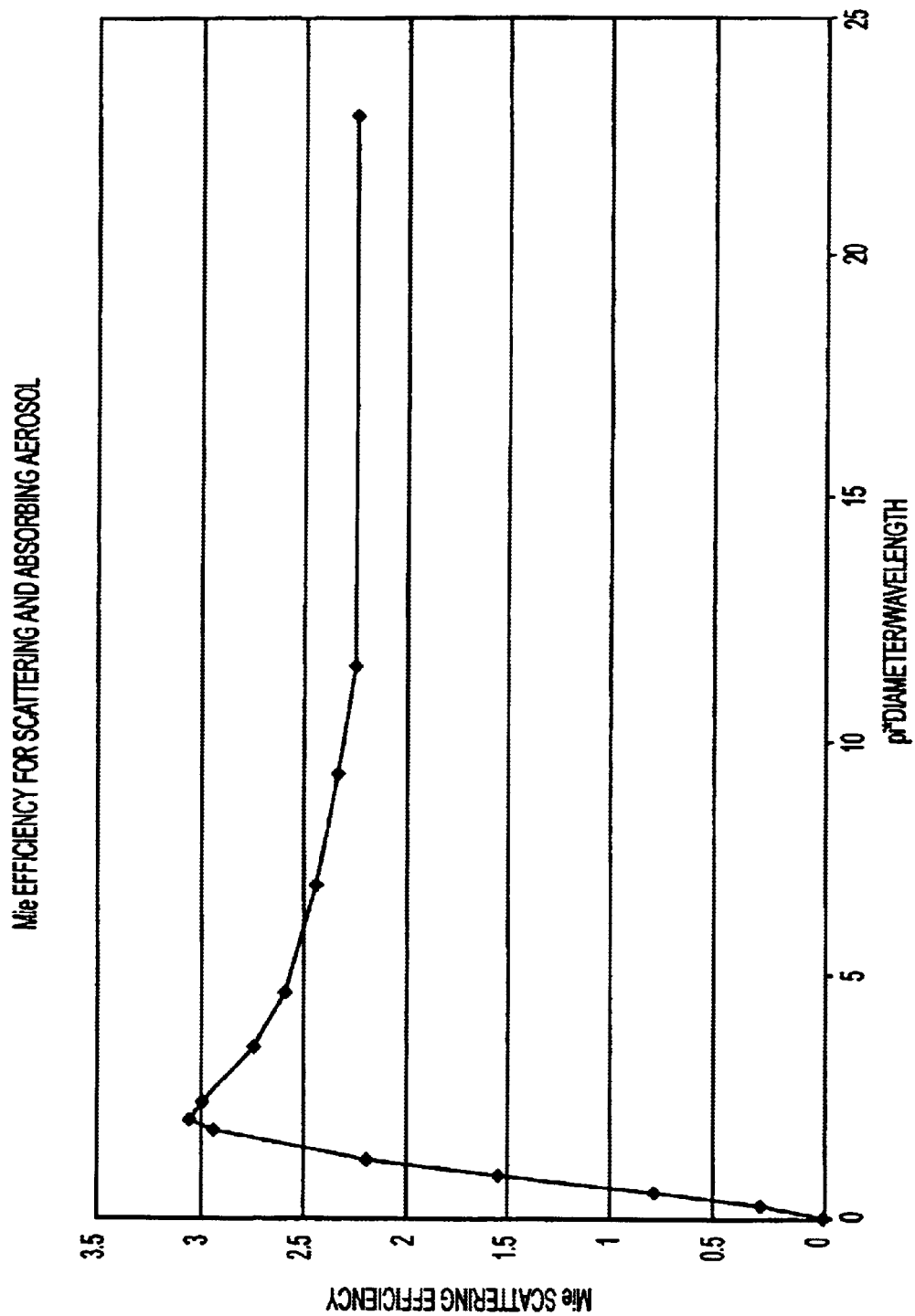
FIG. 3 is a graph of Mie scattering data presented by Bohren and Huffman, 1983.

An approximation of the Mie scattering data presented by Bohren and Huffman, 1983, is shown in FIG. 3, and was used for the calculations.

From the experimentally measured UV and IR signals, the mean particle diameter can be determined using the data represented graph of FIG. 2. This example used 0.23 microns and 1.6 microns wavelengths, but any number of different wavelengths can be used to determine the various particle size ranges. It is recognized that, in practice, the data of FIGS. 2 and 3 are stored in and calculated by the digital processor 36.

Another useful quantity is a particle size index, $P_s$. This index can be calculated from the measured ultraviolet and infrared signals, and is expressed by $P_s = 1 - 1/R$, that is, subtracting the ratio of the density of the particles in the exhaust whose diameter is greater than the wavelength of said infrared light divided by the density of the particles in the exhaust whose diameter is greater than the wavelength of said ultraviolet light from one. The particle size index, $P_s$, can be used as an indicator of the relative amount of harmful small particulates in the exhaust plume.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. An apparatus for determining the particulate content of an exhaust plume of a vehicle, comprising:

an ultraviolet light source for propagating through the exhaust plume ultraviolet light having a predetermined ultraviolet wavelength;

an infrared light source for propagating through the exhaust plume infrared light;

an ultraviolet light detector for receiving said ultraviolet light after passing through the exhaust plume and producing an ultraviolet signal representative of the reduction in intensity of said predetermined wavelength of ultraviolet light due to scattering by particles whose diameter is greater than said predetermined ultraviolet wavelength;

an infrared detector for receiving said infrared light after passing through the exhaust plume and producing an infrared signal representative of the reduction in intensity of the infrared light; and a processor for determining from the ultraviolet signal the density of particles in the exhaust plume whose diameter is greater than said predetermined wavelength of ultraviolet light, and for determining from the infrared signal the density of carbon dioxide in the exhaust plume, said processor determining the particulate content of the exhaust plume by computing the ratio of the density of the particles whose diameter is greater than said predetermined wavelength of ultraviolet light to the density of the carbon dioxide.

2. The apparatus of claim 1, wherein said predetermined wavelength of the ultraviolet light is about 0.23 microns.

3. The apparatus of claim 1, further comprising a reference cell filled with a known quantity of carbon dioxide, and a reference cell detector for determining the reduction in intensity of a portion of said infrared light as different wavelengths are propagated through the reference cell, said reduction in intensity being due to absorption by carbon dioxide.

4. The apparatus of claim 3, wherein said infrared light source can be tuned to propagate infrared light of various wavelengths, and said infrared detector can produce signals representative of the reduction in intensity of the various wavelengths of infrared light that is propagated through the exhaust plume.

5. The apparatus of claim 4, wherein said processor calculates from the infrared intensities measured at various wavelengths the density produced by said infrared light source of the carbon dioxide in the exhaust plume and calculates as the particulate content, the ratio of the density of the particles whose diameter is greater than said predetermined ultraviolet wavelength to the density of the carbon dioxide, the ratio being characteristic of the relative density of the respective particles.

6. The apparatus of claim 5, wherein said processor calculates as another measure of particulate content, the ratio of the density of the particles whose diameter is greater than said predetermined infrared wavelength to the density of the carbon dioxide, the ratio being characteristic of the relative density of the respective particles.

7. The apparatus of claim 6, wherein said processor calculates the average diameter of particles in the exhaust plume from the value of the particulate content ratio for the ultraviolet light divided by the particulate content ratio for the infrared light.

8. The apparatus of claim 1, wherein said predetermined wavelength of ultraviolet light is about 0.23 microns and said predetermined wavelength of infrared light is about 1.6 microns.

9. The apparatus of claim 1, wherein said predetermined wavelength of ultraviolet light is chosen so as to propagate through the exhaust plume without significant absorption.

10. A method of determining the particulate content of an exhaust plume of a vehicle, comprising:

propagating through the exhaust plume ultraviolet light having a predetermined wavelength;

propagating through the exhaust plume infrared light;

producing from ultraviolet light propagated through the exhaust plume an ultraviolet signal representative of the reduction in intensity of the ultraviolet light due to scattering by particles in the exhaust whose diameter is greater than the ultraviolet wavelength;

producing from infrared light propagated through the exhaust plume an infrared signal representative of the reduction in intensity of the infrared light in the exhaust;

determining from the ultraviolet signal the density of particles in the exhaust plume whose diameter is greater than said predetermined wavelength of the ultraviolet light;

determining the density of carbon dioxide in the exhaust plume; and determining the particulate content of the exhaust plume by computing the ratio of the density of the particles whose diameter is greater than said predetermined wavelength of ultraviolet light to the density of the carbon dioxide.

11. The method of claim 10, further comprising providing a reference cell with a known quantity of carbon dioxide, and determining the reduction in intensity of a portion of said infrared light as different wavelengths are propagated through the reference cell, said reduction in intensity being due to absorption by carbon dioxide.

12. The method of claim 11, further comprising propagating infrared light of various wavelengths through the exhaust plume and producing signals representative of the reduction in intensity of the various wavelengths of infrared light.

13. The method of claim 12, further comprising calculating from the infrared intensities measured at various wavelengths produced by said infrared light source the density of carbon dioxide in the exhaust plume and calculating the ratio of the particles whose diameter is greater than said predetermined ultraviolet wavelength to the density of the carbon dioxide, said ratio of the intensities being characteristic of the relative density of the particles.

14. The method of claim 13, further comprising calculating as another measure of particulate content the ratio of the density of the particles whose diameter is greater than said predetermined infrared wavelength to the density of the carbon dioxide, the ratio being characteristic of the relative density of the respective particles.

15. The method of claim 14, further comprising calculating the average diameter of particles in the exhaust plume from the value of the particulate content ratio for the ultraviolet light divided by the particulate content ratio for the infrared light.

16. The method of claim 10, where in the predetermined wavelength of light is about 0.23 microns and said predetermined wavelength of infrared light is about 1.6 microns.

17. The method of claim 10, wherein said predetermined wavelength of ultraviolet light is chosen so as to propagate through the exhaust plume without substantial absorption.

18. An apparatus for determining the particulate content of an exhaust plume of a vehicle, comprising:

an infrared light source for propagating infrared light through the exhaust plume;

an infrared detector for receiving said infrared light after passing through the exhaust plume and producing an infrared signal representative of the reduction in intensity of the infrared light; and a processor for determining from the infrared signal the density of particles in the exhaust plume whose diameter is greater than said predetermined wavelength of infrared light and the density of carbon dioxide in the exhaust, said processor determining the particulate content by computing the ratio of the density of the particles in the exhaust plume whose diameter is greater than said predetermined wavelength of infrared light to the density of the carbon dioxide.

19. The apparatus of claim 18, further comprising a reference cell filled with a known quantity of carbon dioxide, and a reference cell detector for determining the reduction in intensity of a portion of said infrared light propagated through the reference cell at various wavelengths, said reduction in intensity being due to absorption by carbon dioxide.

20. The apparatus of claim 19, wherein said infrared light source can be tuned to propagate infrared light of various wavelengths, and said infrared detector can produce signals representative of the reduction in intensity of the various wavelengths of infrared light that is propagated through the exhaust plume.

21. The apparatus of claim 20, wherein said processor calculates from infrared intensities measured at various wavelengths produced by said infrared light source the density of the carbon dioxide in the exhaust plume.

22. A method of determining the particulate content of an exhaust plume of a vehicle, comprising:

propagating through the exhaust plume infrared light;

producing from infrared light propagated through the exhaust plume an infrared signal representative of the reduction in intensity of the infrared light in the exhaust plume;

determining the density of carbon dioxide in the exhaust plume; and determining the particulate content of the exhaust plume by computing the ratio of the density of the particles whose diameter is greater than said predetermined wavelength of infrared light to the density of the carbon dioxide.

23. The method of claim 22, further comprising providing a reference cell with a known quantity of carbon dioxide, and determining the reduction in intensity of a portion of said infrared light as different wavelengths are propagated through the reference cell, said reduction in intensity being due to absorption by carbon dioxide.

24. The method of claim 23, further comprising propagating infrared light of various wavelengths through the exhaust plume and producing signals representative of the reduction in intensity of the various wavelengths of infrared light.

25. The method of claim 24, further comprising calculating from the infrared intensities measured at various wavelengths produced by said infrared light source the density of carbon dioxide in the exhaust plume and calculating the ratio of the particles whose diameter is greater than said predetermined infrared wavelength to the density of the carbon dioxide, said ratio of the intensities being characteristic of the relative density of the particles.

26. An apparatus for determining the average size of particles in an exhaust plume of a vehicle, comprising:
an ultraviolet light source for propagating through the exhaust plume ultraviolet light having a predetermined ultraviolet wavelength;
an infrared light source for propagating through the exhaust plume infrared light;
an ultraviolet light detector for receiving said ultraviolet light after passing through the exhaust plume and producing an ultraviolet signal representative of the reduction in intensity of said predetermined wavelength of ultraviolet light due to scattering by particles whose diameter is greater than said predetermined ultraviolet wavelength;
an infrared detector for receiving said infrared light after passing through the exhaust plume and producing an infrared signal representative of the reduction in intensity of the infrared light; and
a processor for determining from the ultraviolet signal the density of particles in the exhaust plume whose diameter is greater than said predetermined wavelength of ultraviolet light, and for determining from the infrared signal the density of particles in the exhaust plume whose diameter is greater than said predetermined wavelength of infrared light, said processor determining the average diameter of the particles in the exhaust.

27. The apparatus of claim 26, wherein said predetermined wavelength of the ultraviolet light is substantially about 0.23 microns.

28. The apparatus of claim 26, further comprising a reference cell filled with a known quantity of a predetermined substance, and a reference cell detector for determining the reduction in intensity of a portion of said infrared light propagated through the reference cell at various wavelengths, said reduction in intensity being due to absorption by the predetermined substance.

29. The apparatus of claim 28, wherein said infrared light source can be tuned to propagate infrared light of various wavelengths, and said infrared detector can produce signals representative of the reduction in intensity of the various wavelengths of infrared light that is propagated through the exhaust plume.

30. The apparatus of claim 29, wherein said processor calculates from infrared intensities measured at various wavelengths produced by said infrared source the density of the predetermined substance and the density of particles whose diameter is greater than said predetermined infrared wavelength, and calculates as a first measure of particulate content, the ratio of the density of the particles whose diameter is greater than said predetermined ultraviolet wavelength to the density of the predetermined substance, and as a second measure of particulate content, the ratio of the density of the particles whose diameter is greater than said predetermined infrared wavelength to the density of the predetermined substance, the ratio being characteristic of the diameter of the particles.

31. The apparatus of claim 30, wherein said processor calculates from a ratio of the first measure of particulate content to the second measure of particulate content the average diameter of the particles in the exhaust plume.

32. The apparatus of claim 26, wherein said predetermined wavelength of ultraviolet light is about 0.23 microns and said predetermined wavelength of infrared light is about 1.6 microns.

33. The apparatus of claim 26, wherein said predetermined wavelength of ultraviolet light is chosen so as to propagate through the exhaust plume without significant absorption.

34. The apparatus of claim 26, wherein the predetermined substance is carbon dioxide.

35. The apparatus of claim 26, wherein said processor calculates a particle size index by subtracting the ratio of the density of the particles in the exhaust plume whose diameter is greater than the wavelength of said infrared light to the density of the particles in the exhaust plume whose diameter is greater than the wavelength of said ultraviolet light from one.

36. A method of determining the average diameter of particles in an exhaust plume of a vehicle, comprising:
propagating through the exhaust plume ultraviolet light having a predetermined ultraviolet wavelength;
propagating through the exhaust plume infrared light;
producing from ultraviolet light propagated through the exhaust plume an ultraviolet signal representative of the reduction in intensity of the ultraviolet light due to scattering by particles in the exhaust whose diameter is above the ultraviolet wavelength;
producing from infrared light propagated through the exhaust plume an infrared signal representative of the reduction in intensity of the infrared light in the exhaust;
determining from the ultraviolet signal the density of particles in the exhaust plume whose diameter is greater than said predetermined wavelength of ultraviolet light;
determining from the infrared signal the density of the particles whose diameter is greater than said predetermined infrared wavelength; and
determining the average diameter of particles in the exhaust plume by computing the ratio of the density of the particles whose diameter is greater than said predetermined wavelength of ultraviolet light to the density of the particles whose diameter is greater than said predetermined wavelength of infrared light.

37. The method of claim 36, further comprising providing a reference cell with a known quantity of a predetermined substance, and determining the reduction in intensity of a portion of said infrared light as different wavelengths are propagated through the reference cell, said reduction in intensity being due to absorption by the predetermined substance.

38. The method of claim 37, further comprising propagating infrared light of various wavelengths through the exhaust plume, and producing signals representative of the reduction in intensity of the various wavelengths of infrared light.

39. The method of claim 38, further comprising calculating from infrared intensities measured at various wavelengths produced by said infrared source the density of the predetermined substance and the density of particles whose diameter is greater than said predetermined infrared wavelength, and calculating, as a first measure of particulate content, the ratio of the density of the particles whose diameter is greater than said predetermined ultraviolet wavelength to the density of the predetermined substance, and as a second measure of particulate content, the ratio of the density of the particles whose diameter is greater than said predetermined infrared wavelength to the density of the predetermined substance, the ratio being characteristic of the diameter of the particles.

40. The method of claim 39, further comprising calculating from the ratio of a first measure of particulate content to the second measure of particulate content the average diameter of the particles in the exhaust plume.

41. The method of claim 36 wherein said predetermined wavelength of ultraviolet light is about 0.23 microns and said predetermined wavelength of infrared light is about 1.6 microns.

42. The method of claim 36, wherein said predetermined wavelength of the ultraviolet light is chosen so as to propagate through the exhaust plume without substantial absorption.

43. The method of claim 36, wherein said predetermined substance is carbon dioxide.

44. The method of claim 36, further comprising, calculating a particle size index by subtracting the ratio of the density of the particles in the exhaust plume whose diameter is greater than the wavelength of said infrared light divided to the density of the particles in the exhaust plume whose diameter is greater than the wavelength of said ultraviolet light from one.

* * * * *